United States Patent
Raje et al.

(10) Patent No.: US 10,588,777 B2
(45) Date of Patent: Mar. 17, 2020

(54) INTRAUTERINE DEVICE WITH A RESTRICTED MOVEMENT OF A STRING KNOT

(71) Applicant: PREGNA INTERNATIONAL LIMITED, Mumbai, Maharashtra (IN)

(72) Inventors: Ajit Raje, Maharashtra (IN); Usha Kumar, London (GB)

(73) Assignee: Pregna International Limited, Mumbai (IN)

( * ) Notice: Subject to any disclaimer, the term of this patent is extended or adjusted under 35 U.S.C. 154(b) by 388 days.

(21) Appl. No.: 15/519,173

(22) PCT Filed: Dec. 23, 2014

(86) PCT No.: PCT/IN2014/000796
§ 371 (c)(1),
(2) Date: Apr. 14, 2017

(87) PCT Pub. No.: WO2016/059640
PCT Pub. Date: Apr. 21, 2016

(65) Prior Publication Data
US 2017/0231809 A1    Aug. 17, 2017

(30) Foreign Application Priority Data

Oct. 17, 2014  (IN) .......................... 3319/MUM/2014

(51) Int. Cl.
*A61F 6/18* (2006.01)
*A61F 6/14* (2006.01)

(52) U.S. Cl.
CPC ................ *A61F 6/18* (2013.01); *A61F 6/142* (2013.01); *A61F 6/144* (2013.01)

(58) Field of Classification Search
CPC ....... A61F 6/144; A61F 6/142; A61K 9/0039; A61K 9/0036; A61M 31/002
See application file for complete search history.

(56) References Cited

FOREIGN PATENT DOCUMENTS

WO    WO-2014023797 A1 *   2/2014   ........... A61K 9/0039

\* cited by examiner

*Primary Examiner* — Ophelia A Hawthorne

(57) ABSTRACT

An intrauterine device (20) with a restricted movement of a knot (5) of the string (4) due to a region (3) having such differed shape and size at a distal end (12) of central vertical stem (1) and due to a trajectory for string (4) in the region (3) that the length of the string (S) is shorter than the distance (r) of the region (3); and the loop (15) of the string and therefore the knot (5) is unable to pivot around the axis (14). The lateral shift of the knot (5) is also prevented. Consequent to restricted pivoting and restricted lateral shift of the knot (5), the hanging portion (9) of the string (4) continue to project downwards and do NOT develop tendency to get retracted and thus do not curl up in the uterus (16) through the cervix (17).

7 Claims, 25 Drawing Sheets

INTRAUTERINE DEVICE WITH A RESTRICTED MOVEMENT OF A STRING KNOT

FIELD OF THE INVENTION

This invention relates to the intrauterine device (IUD) and particularly to an IUD with string. More particularly, the invention relates to an IUD with a knotted string. Still more particularly, the invention relates to prevent curling up of the knotted string of the IUD.

BACKGROUND OF THE INVENTION

An intrauterine device (IUD) is a birth control device, which is placed in the uterus of a woman. IUDs have been known since several decades, and are popularly known as "Copper-T". IUDs are of different types viz. copper IUD, hormonal IUD, etc. and are available in various shapes, for example T-shaped, and sized to fit inside the uterus of women.

IUDs currently in the market are generally provided with one or more strings extending from the bottom of the IUD. When the IUD is placed in the uterus, the string(s) extend through the cervix and remain positioned in the vaginal cavity, such that a woman can "feel" the presence of string(s) by her finger.

IUD being a foreign matter in the body, there are possibilities that the IUD gets expelled from the uterus/body of the woman. Such expulsion can happen during menstrual cycle for example. Women are advised to "feel" the presence of the string(s) after every menstrual cycle so as to be assured of presence of the contraceptive device. String(s) are also helpful for pulling the IUD out of the uterus when the IUD is required to be removed. U.S. Pat. No. 3,902,483 describes an intrauterine device having two threads, a locator thread and a reserve thread. If women do not find the string, it makes them anxious that IUD has possibly got expelled and they are without protection.

Besides IUD getting expelled, there are many possible reasons for string not in place. One of the reasons that has lately come to the knowledge is that strings are not in place although the IUD is in situ; because—the strings are curled up and retracted into the endocervical canal or uterine cavity. U.S. Pat. Nos. 4,372,302 and 4,561,433 recognize this problem and describe instruments for retrieval of the retracted threads or strings of the IUD. These patents, however, do not address the cause and solution of the problem of curling/retracting.

Patent Publication Number EP0179518A1 describes an IUD extractor thread where an IUD is provided with an extractor thread and such thread is coated with metallic silver which helps in preventing the bacteriological infections which occur due to the normal threads of IUD. Although this invention deals with the IUD threads, but does not address curling.

Patent Publication Number U.S. 20110247630 describes an intrauterine device with string divided into upper, intermediate and lower portion. The upper portion is configured to attach to the stem of IUD. Intermediate portion runs through the endocervical canal and the lower portion follows the contour of the cervix. The disclosure is silent about string curling. The lower portion comprising a curved portion is configured to follow a contour of the external orifice of the cervix; and therefore, this method may prevent up curling of string, however, the procedure is painful, complex and intervening with active life of the women and her partner; and therefore is impractical.

One of the common ways to attach the string to the IUD frame is by having a through-hole at the lower end of the IUD frame and tying the string by way of a knot. Patent application Number U.S. 2013/0298361A1 describes the knotting method. This disclosure is more towards achieving productivity rather than addressing said problem.

As can be easily appreciated, there is no prior invention which addresses the problem related to curling or retraction of knotted strings.

Our invention addresses the cause of curling and or retracting of knotted strings and solves this problem.

OBJECTIVE OF THE INVENTION

The objective of the invention is to provide an intrauterine device wherein the knotted string does not retract into the cervical canal of the female.

Another objective of the invention is to provide an intra-uterine device which is not unduly different in construction than current devices.

Yet another objective is to invent an intrauterine device with ease of manufacturing and the end product being economical.

Yet another objective of the invention is to provide an intrauterine device which is hygienic, safe and proven for inserting in the uterus of the female as current devices.

SUMMARY OF THE INVENTION

Our invention deals with an intrauterine device with restricted undesired curling of the string. T-shaped IUD is considered for disclosure of our invention, however, the shape of the IUD is not a limitation and this invention pertains to IUDs of all shapes and type, whether copper or hormonal or medicinal, with the knotted string.

An intrauterine device described here comprises of a central vertical stem having a pair of arms attached at a proximal end and a spherical bulge at a distal end.

A string is passed through a through-hole provided in the spherical bulge. A knot of the string is tied in the vicinity of the spherical bulge, leaving a hanging portion of the string free. Due to the spherical bulge and the through-hole, a length of the string (S) is invariably longer than a radius (r) of the spherical bulge; and a loop of the string, and therefore the knot is free to pivot around an axis and take an upward position termed as a lateral shift of the knot.

In our invention, there is a region at the distal end of the central vertical stem; the region has passage for the string called a trajectory, which is a defined as a route through and or alongside which the string and the knot is contained. The trajectory is a combination of a plurality of closed channel, a plurality of open channel, a plurality of open recess, a plurality of opening and a plurality of orifice, present in or on the region at the distal end of the IUD. The string is laid through the trajectory and the knot is tied keeping the string taut. Consequent to the region and the trajectory, the knot is restricted from pivoting around the openings(s) and also the lateral shift towards the facilitating opening(s) is constrained.

Due to restricted movement viz. pivoting and lateral shifting of the knot, the tendency of the string to curl up and thereby retract into cervix is prevented.

The hanging portion of the string after knotting remains free. Once the IUD is placed in the uterus, the strings continue to project out of the cervix into the vaginal cavity and remain available for feel and verification of presence, as also to facilitate removal of IUD.

DETAILED DESCRIPTION OF THE INVENTION

Figure 1A:
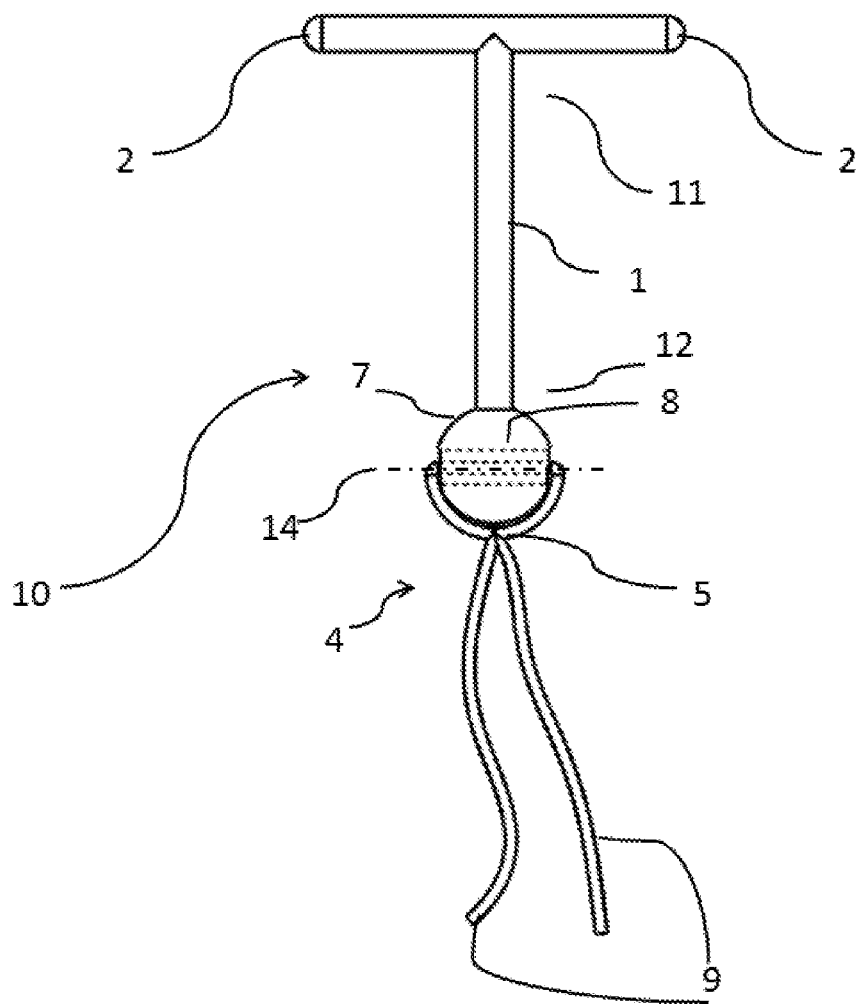
FIG. 1A illustrates by front view an IUD with a spherical bulge, a string and a loop of the string.

Preferred embodiment of the Intrauterine Device with a restricted movement of a string knot according to present invention will now be described in detail, with reference to the accompanying drawings. The terms and expressions which have been used here are merely for description and not for limitation. A "T-shaped" IUD is considered for disclosure of our invention, however, the shape of the IUD is not a limitation and this invention pertains to IUDs of all shapes and type, whether copper or hormonal or medicinal, provided, the IUD has a string which is knotted.

FIG. 1A, 1B, 1C, 1D and 1E describe the prior art. As can be seen from FIG. 1A, a prior art intrauterine device (10) comprises a central vertical stem (1) having a pair of arms (2) attached at a proximal end (11) and a spherical bulge (7) at a distal end (12). A string (4) is passed through a through-hole (8) provided in the spherical bulge (7). A knot (5) of the string (4) is tied in the vicinity of the spherical bulge (7), leaving a hanging portion (9) of the string (4) free.

Figure 1B:
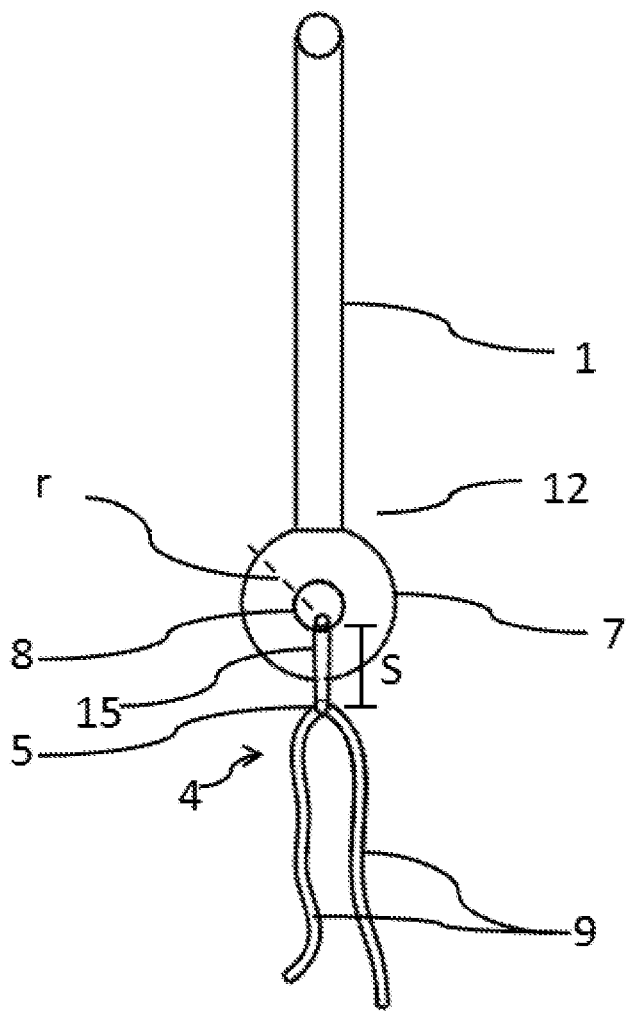
FIG. 1B illustrates by side view a string passing through the through-hole in the spherical bulge; and the loop of the string.
Figure 1C:
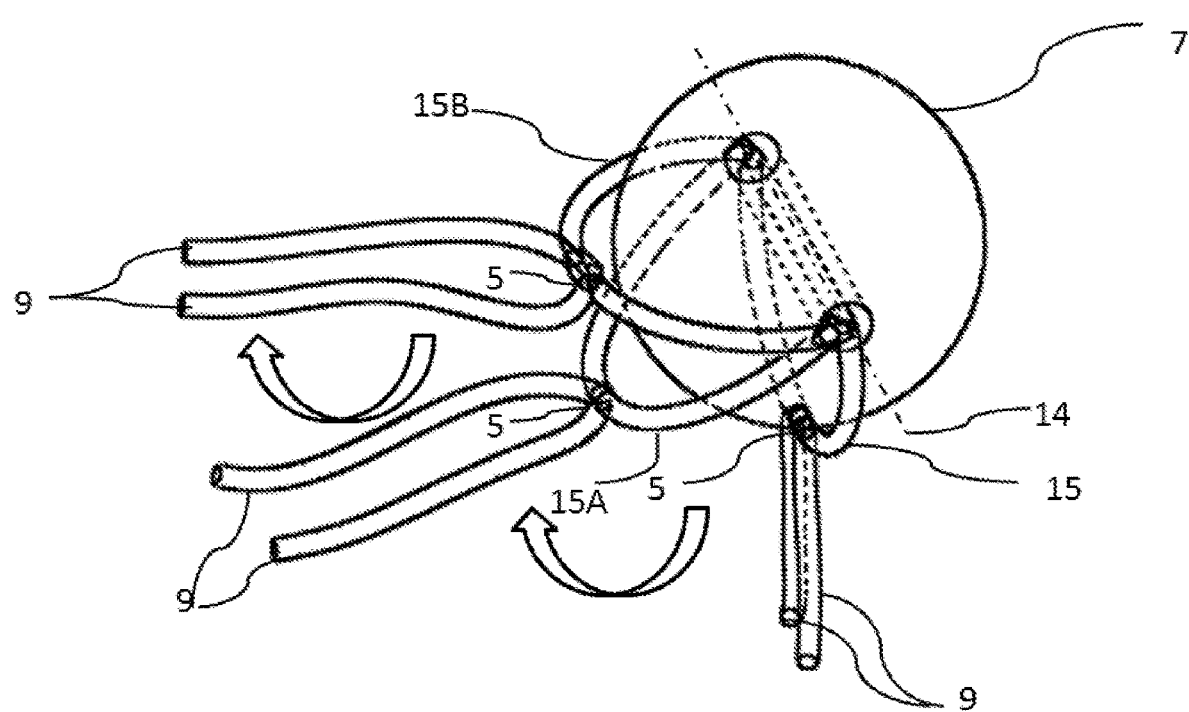
FIG. 1C illustrates pivoting of a loop of the string around the spherical bulge of the IUD, showing the loop of the string in different positions.

Consequent to the spherical bulge (7) and the through-hole (8), a length of the string (S) is invariably longer than a radius (r) of the spherical bulge (7); and a loop (15) of the string, and therefore the knot (5) is free to pivot around an axis (14) and take an upward positions (15A), (15B), as shown in FIG. 1B, 1C.

Figure 1D:
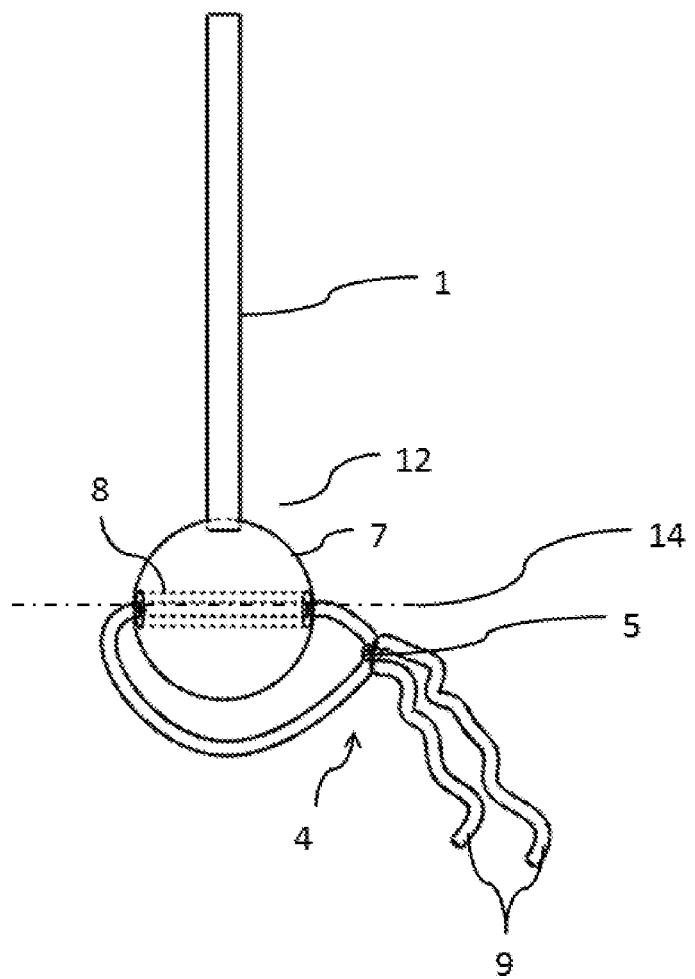
FIG. 1D illustrates the lateral shift of the knot from the position below the spherical bulge of the IUD towards the through-hole.

Also, the knot (5) is free to move from a position below the spherical bulge (7) to a side wards as shown in FIG. 1D. This is termed as a lateral shift of the knot (5).

Figure 1E:
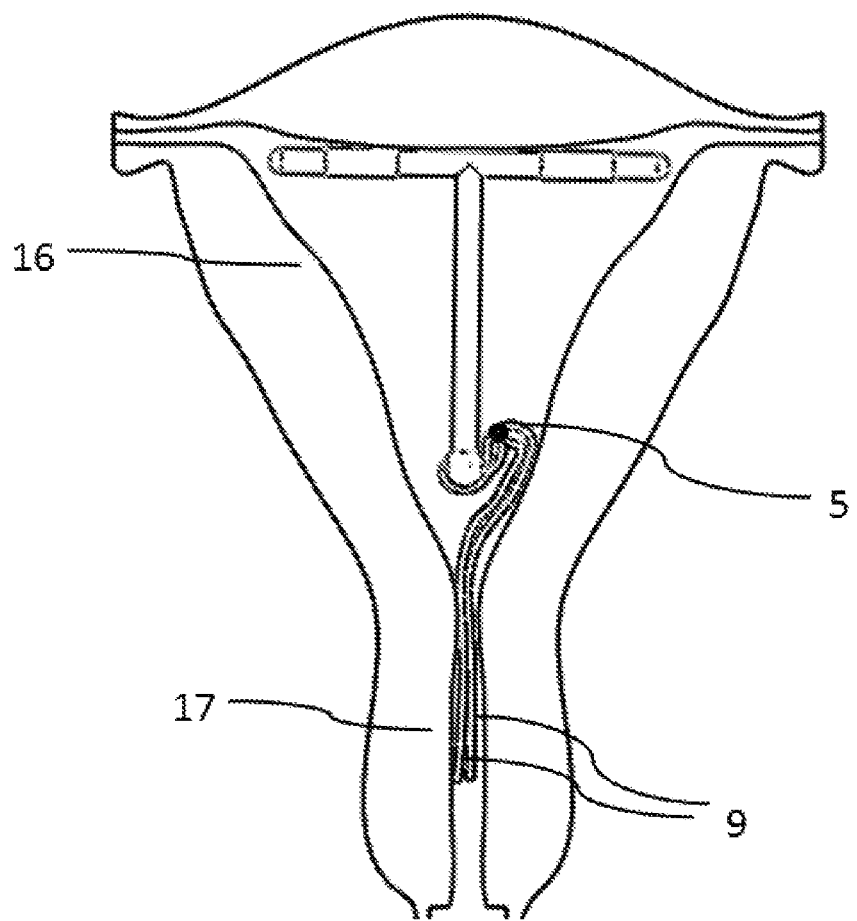
FIG. 1E illustrates the string when retracting in the uterus through the cervix and therefore not coming out of the cervical os.

Consequent to the lateral shift of the knot (5), the hanging portion (9) of the string (4) gets initially pulled and progressively develops tendency to get retracted and thus curl up in the uterus (16) through the cervix (17). FIG. 1E illustrates this situation.

FIG. 2A, 3A, 4A, 5A show embodiments of an intrauterine device (IUD) (20) with a restricted movement of a knot (5) according to present invention. The central vertical stem (1) with the plurality of arms (2) is attached to the proximal end (11) of the central vertical stem (1) as is known. In our invention, there is a region (3) at the distal end (12) of the central vertical stem (1). The region (3) has passage for the string (4), now onwards called a trajectory.

The trajectory is a defined route through and or alongside which the string (4) and the knot (5) is contained, and is a combination of a plurality of closed channel, a plurality of open channel, a plurality of open recess, a plurality of opening and a plurality of orifice, present in or on the region (3) at the distal (12) end of the IUD (20). The string (4) is laid through the trajectory and the knot (5) is tied keeping the string (4) taut. Consequent to the region (3) and the trajectory, the knot (5) is restricted from pivoting around the openings(s) and also the lateral shift towards the facilitating opening(s) is constrained.

Consequent to a shape of the region (3) and a shape of the trajectory, the length of the string (S) is invariably shorter than the distance (r) of the region (3); and the loop (15) of the string, and therefore the knot (5) is unable to pivot and or shift laterally.

Figure 2A:
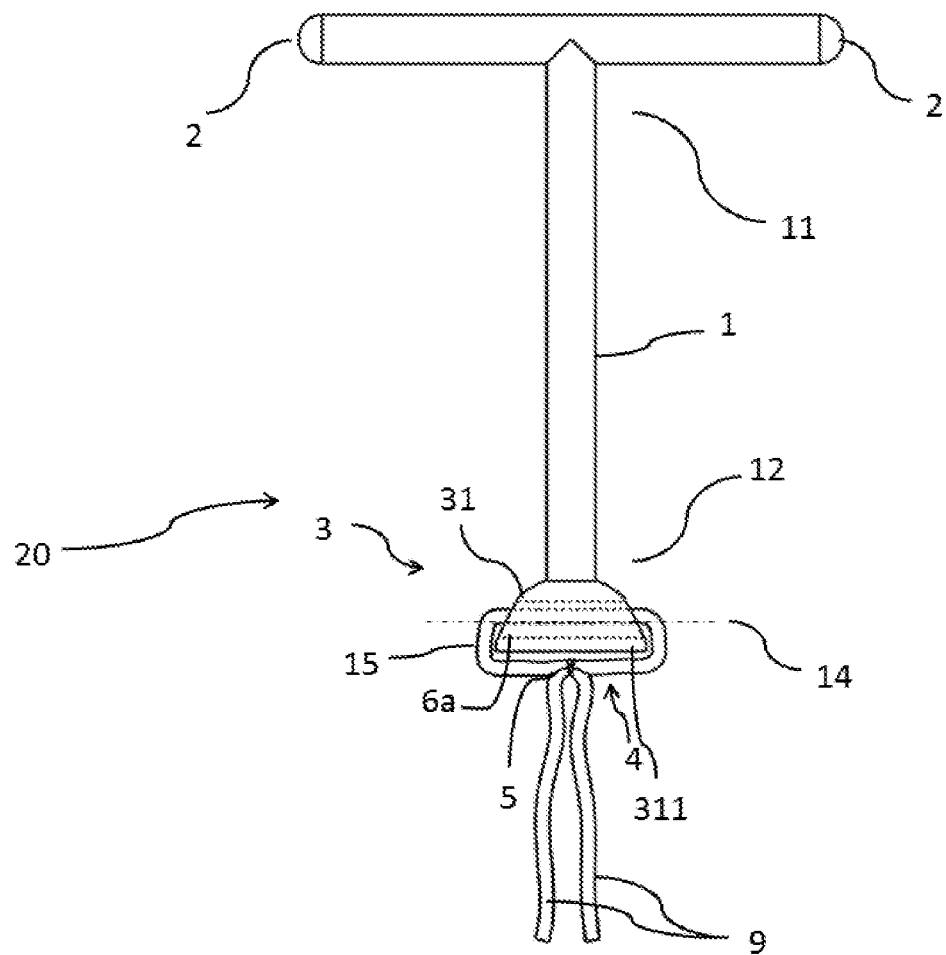
FIG. 2A illustrates an IUD where the region is a hemisphere and a string is passing through a trajectory.
Figure 2B:
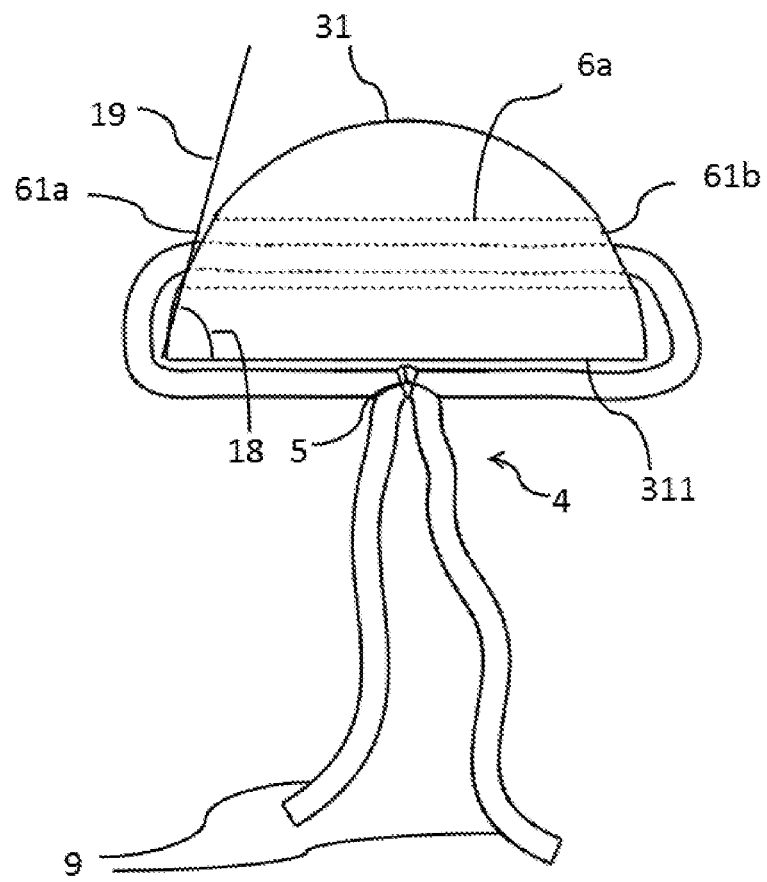
FIG. 2B gives further details of the hemisphere and the trajectory which is a closed channel.
Figure 2C:
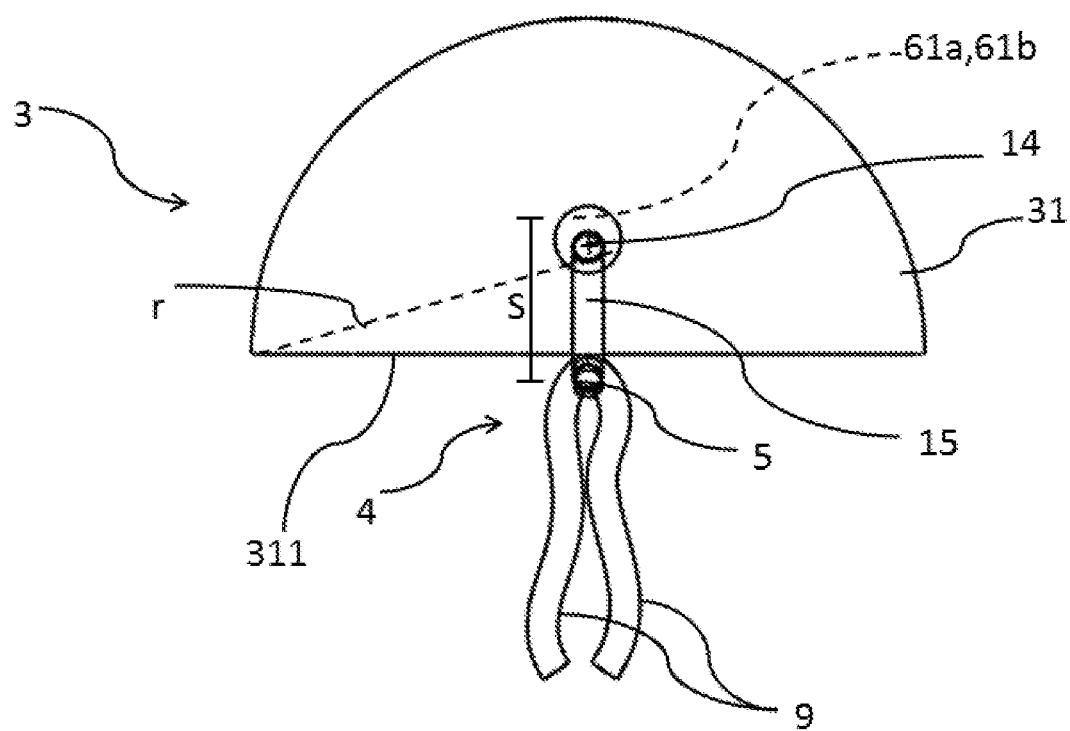
FIG. 2C shows side view of the hemisphere and the loop of the string. Sign of "+" represents an axis which is perpendicular to the plane of this paper.

Referring to FIG. 2A, 2B and 2C, the region (3) is a hemisphere (31) having a flat lower surface (311) perpendicular to the central vertical stem (1). The trajectory is a closed channel (6a) with a pair of openings (61a, 61b) at the ends of the closed channel (6a), provided transversally to the central vertical stem (1) in the hemisphere (31), the axis (14) of the channel (6a) being parallel to the flat lower surface (311) of the hemisphere (31).

The string (4) is passed through a first opening (61a) of the channel (6a) and retrieved from a second opening (61b) of the channel and the knot (5) is tied keeping the string (4) taut, immediately below the flat lower surface (311) of the hemisphere (31) and in the middle, leaving the hanging portion (9) of the strings (4) free.

Consequent to a shape of the hemisphere (31) and the shape of the trajectory, the length of the string (S) is shorter than the distance (r) of the region (3); and the loop (15) of the string and therefore the knot (5) is unable to pivot around the axis (14) as shown in FIG. 2C.

Consequent to the shape of the hemisphere (31), an angle (18) between a plane of the lower surface (311) and a tangent (19) at the end of the hemisphere (31) causes a sharp bend for the string (4) as shown in FIG. 2B. Due to taut tying of the knot while keeping the string (4) taut, and the sharp bend, the knot (5) is NOT free to move from a position below the flat lower surface (311) to the side wards as already shown in FIG. 1D. In other words, the lateral shift of the knot (5) is restricted.

Consequent to restricted pivoting and the lateral shift of the knot (5), the hanging portion (9) of the string (4) continue to project downwards and do NOT develop tendency to get retracted and thus do NOT curl up in the uterus (16) through the cervix (17) as earlier shown in FIG. 1E.

Referring to FIG. 3A, 3B, 3C and 3D, the region (3) is a hemisphere (31) having a flat lower surface (311) perpendicular to the central vertical stem (1) with a plurality of recess (312) present on the flat lower surface (311). The trajectory is a closed channel (6a) with a pair of openings (61a, 61b) at the ends of the closed channel (6a), provided transversally to the central vertical stem (1) in the hemisphere (31), an axis (14) of the channel (6a) being parallel to the flat lower surface (311) of the hemisphere (31).

Figure 3A:
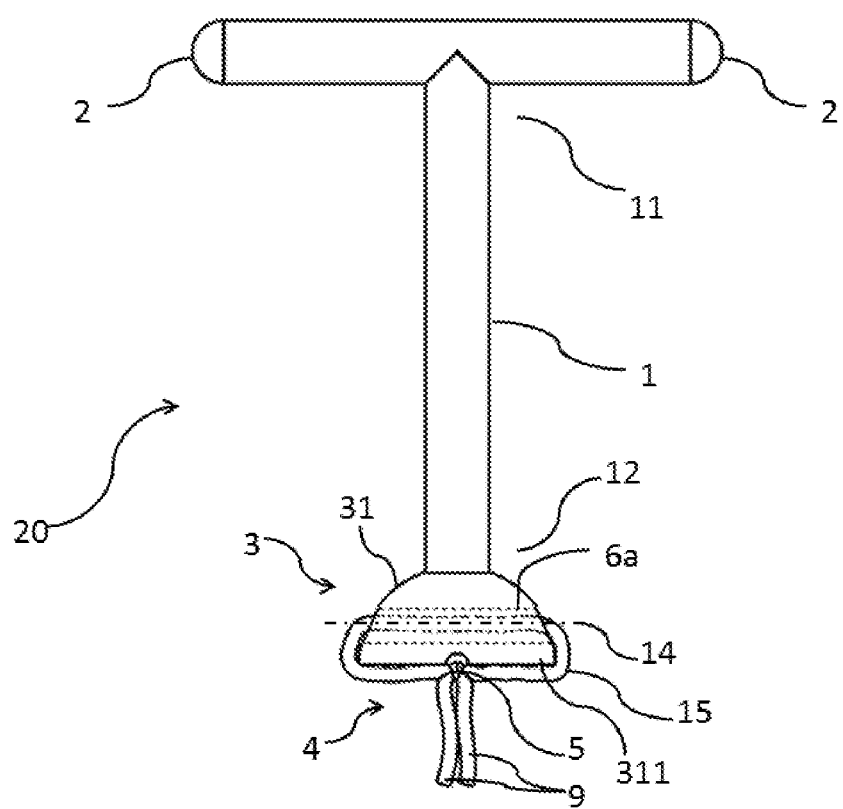
FIG. 3A illustrates IUD where the region is a hemisphere having a recess on the flat lower surface.
Figure 3B:
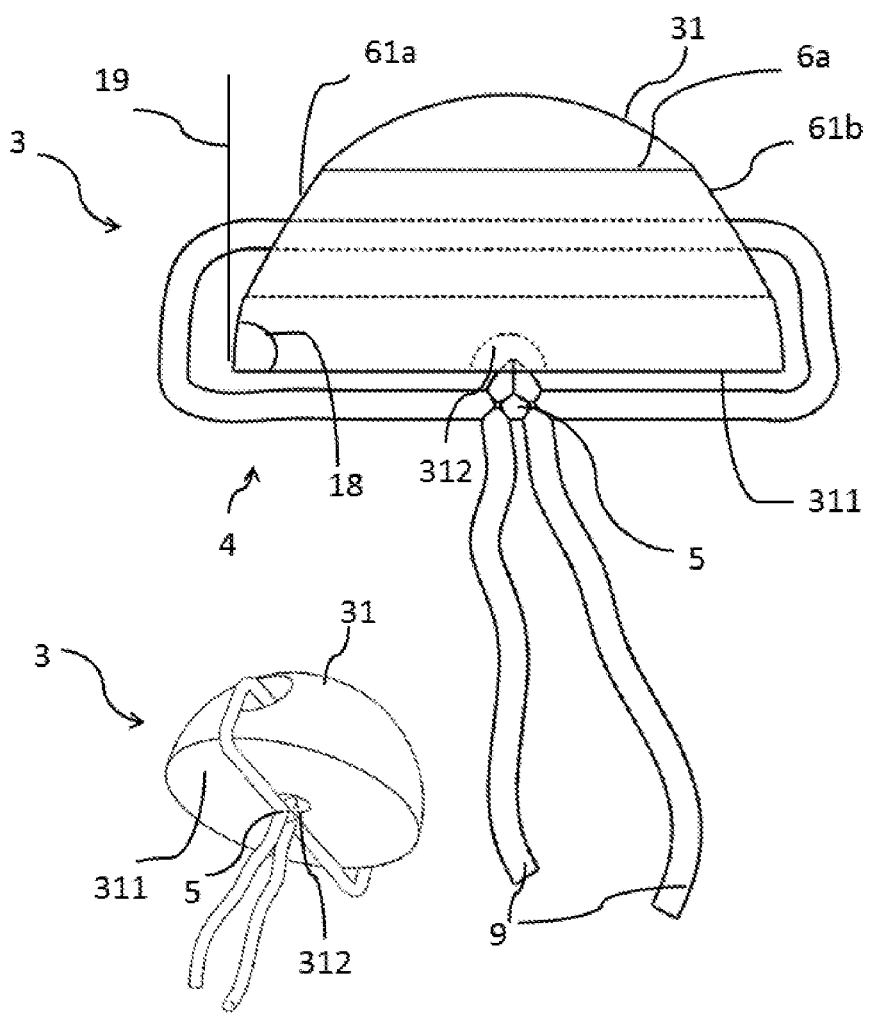
FIG. 3B gives further details of the hemisphere with the recess, and the trajectory which is a closed channel.

The string (4) is passed through a first opening (61a) of the channel (6a) and retrieved from a second opening (61b) of the channel and a knot (5) is tied keeping the string (4) taut immediately below at the flat lower surface (311) of the hemisphere (31) and in the middle, such that the knot (5) rests in the recess (312) provided in the flat lower surface (311) of the hemisphere (31), as shown in FIG. 3B, leaving the hanging portion (9) of the string (4) free.

Figure 3C:
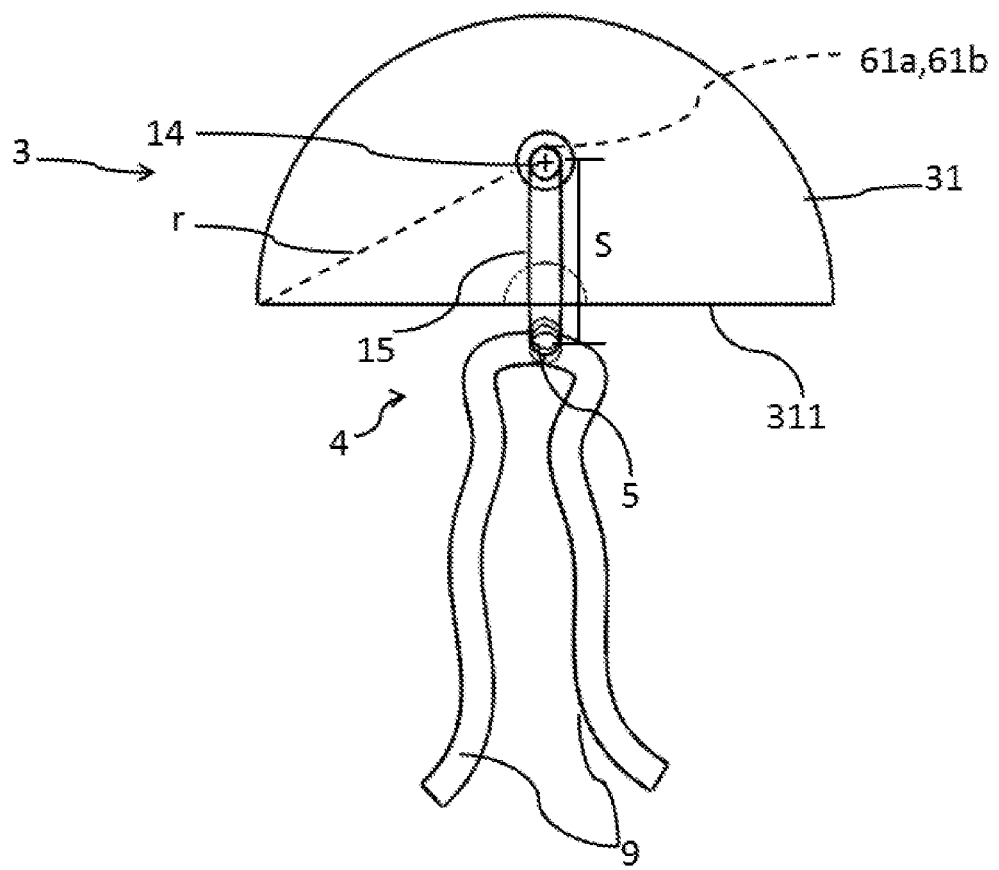
FIG. 3C shows side view of the hemisphere and the loop of the string. Sign of "+" represents an axis which is perpendicular to the plane of this paper.
Figure 3D:
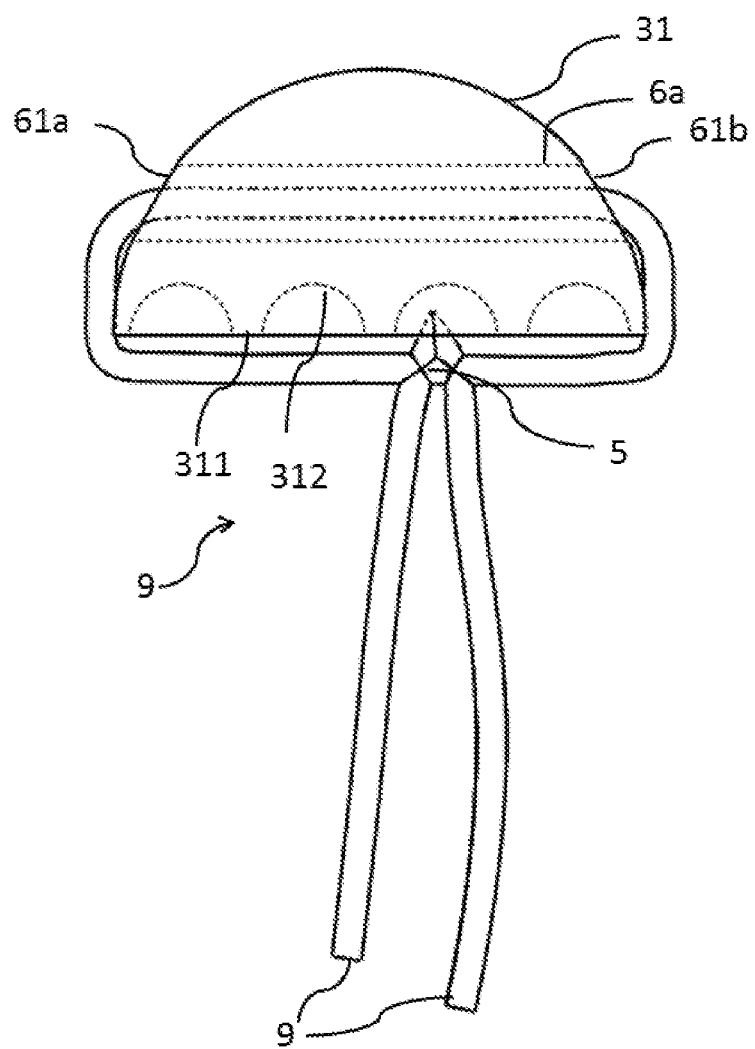
FIG. 3D illustrates the hemisphere having a plurality of recess on the flat lower surface.

Consequent to a shape of the hemisphere (31) and a shape of the trajectory, the length of the string (S) is shorter than the distance (r) of the region (3); and the loop (15) of the string, and therefore the knot (5) is unable to pivot around the axis (14) as shown in FIG. 3C.

Consequent to the shape of the hemisphere (311), an angle (18) between a plane of the flat lower surface (311) and a tangent (19) at the end of the hemisphere (31) causes a sharp bend for the string (4). Due to taut tying of the knot while keeping the string (4) taut, and the sharp bend, the knot (5) is NOT free to move from a position below the flat lower surface (311) to the side wards as shown in FIG. 3B. Further, consequent to the knot (5) resting in the recess (312), the knot (5) is further restricted from moving from the position below the flat lower surface (311) to the side wards as shown in FIG. 1D. In other words, the lateral shift of the knot (5) is restricted.

Consequent to the restricted pivoting and the lateral shift of the knot (5), the hanging portion (9) of the string (4) continue to project downwards and do NOT develop tendency to get retracted and thus do NOT curl up in the uterus (16) through the cervix (17) as shown in FIG. 1E.

Figure 4A:
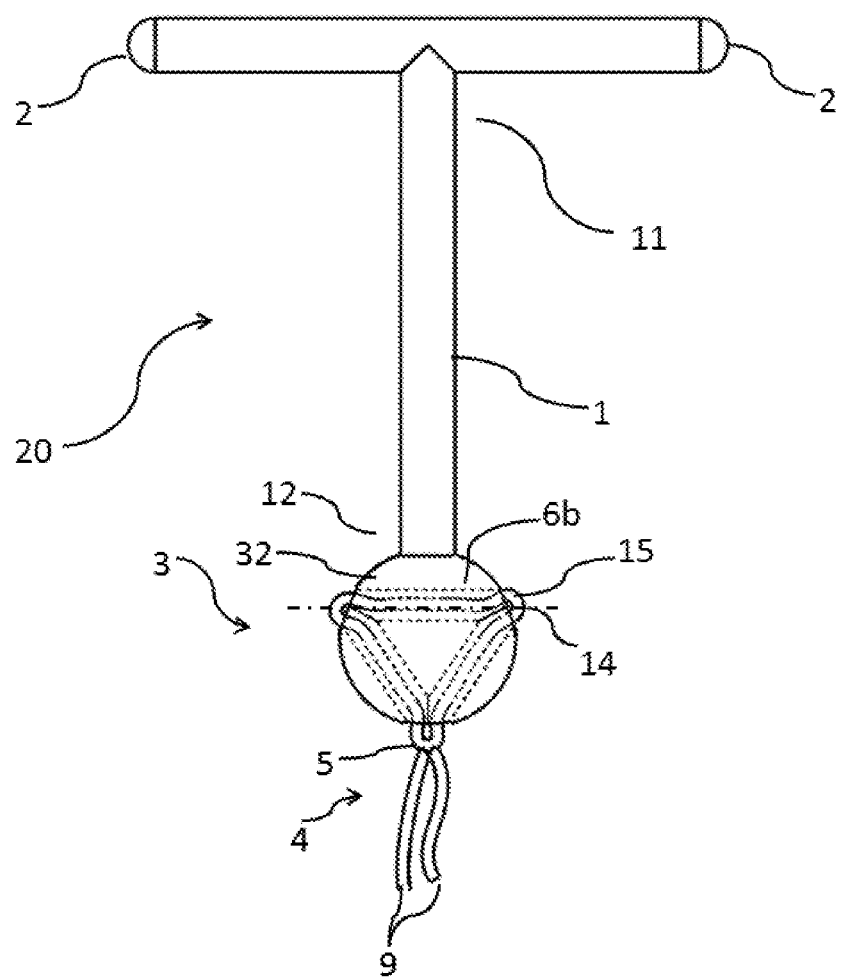
FIG. 4A illustrates IUD where the region is a sphere and trajectory is a triangular closed channel.
Figure 4B:
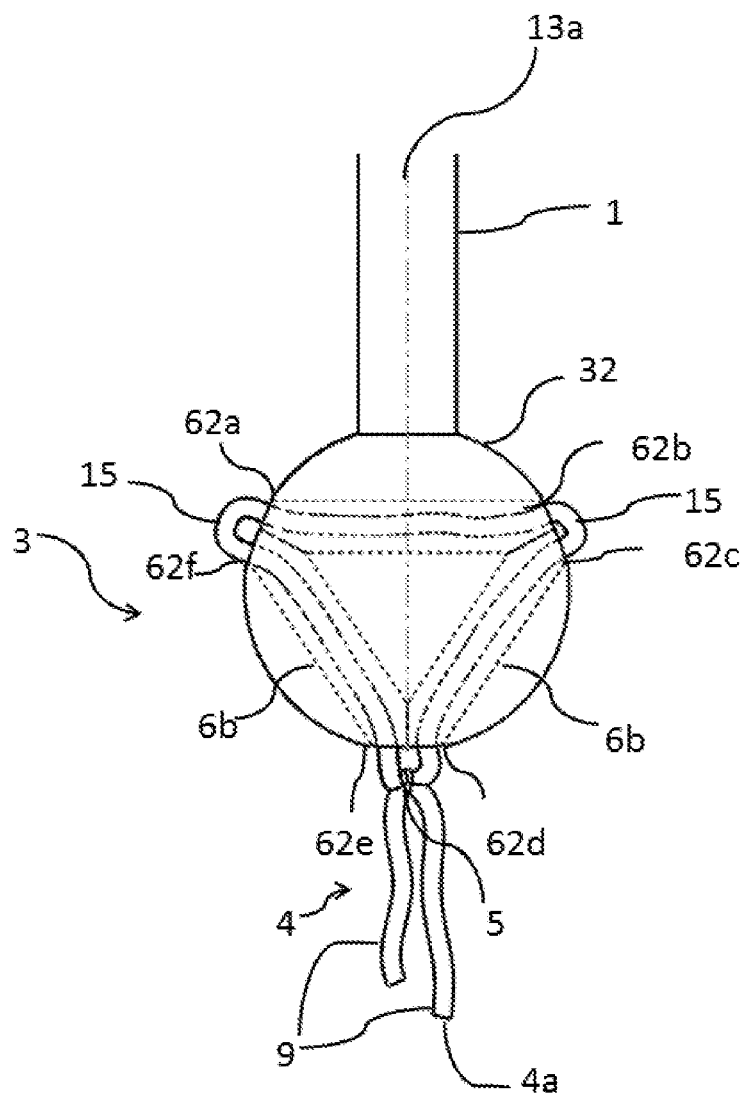
FIG. 4B gives further details of the trajectory and placement of the string in the trajectory.

Referring to FIG. 4A and 4B, the region (3) is a sphere (32) present at the distal end (12) of the central vertical stem (1) of the IUD (20). The trajectory is a triangular closed channel (6b) with a three pairs of openings (62a, 62b), (62c, 62d) and (62e, 62f) at a three ends of the triangular closed channel (6b), an axis (14) of openings (62a, 62b) being transversal to the central vertical stem (1) and a middle of the opening (62e) and opening (62d) substantially in a same axis (13a) as of the central vertical stem (1).

A first end (4a) of the string (4) is passed through the opening (62e) of the triangular closed channel (6b) and retrieved from the opening (62f) of the triangular closed channel (6b). The same first end (4a) of the retrieved string (4) is then passed through the opening (62a) and retrieved from the opening (62b). Finally the same first end (4a) of the retrieved string (4) is passed through the opening (62c) and retrieved from the opening (62d). A knot (5) is tied keeping the string (4) taut immediately in the middle of the opening (62e) and the opening (62d), leaving the hanging portion (9) of the string (4) free.

Figure 4C:
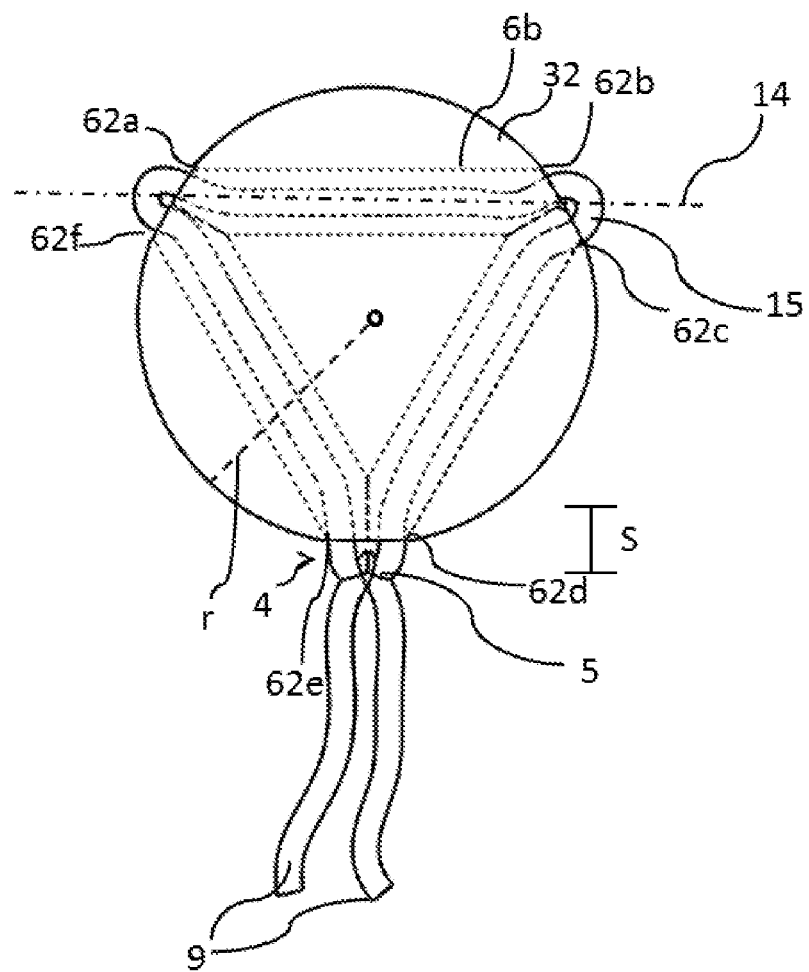
FIG. 4C gives closer view of the triangular closed channel and the string passing through the openings of triangular closed channel.

Consequent to the shape of the sphere (32) and the corresponding trajectory (6b) the length of the string (S) is shorter than the distance (r) of the region (3); and the loop (15) of the string and therefore the knot (5) is unable to pivot around the axis (14) as shown in FIG. 4C.

Consequent to the shape of the sphere (32), and the corresponding trajectory (6b), the knot (5) is NOT free to move from the position in the middle of the opening (62e) and the opening (62d) to the side wards as shown in FIG. 1D. In other words, the lateral shift of the knot (5) is restricted.

Consequent to the restricted pivoting and the lateral shift of the knot (5), the hanging portion (9) of the string continue to project downwards and do NOT develop tendency to get retracted and thus do NOT curl up in the uterus (16) through the cervix (17).

Figure 5A:
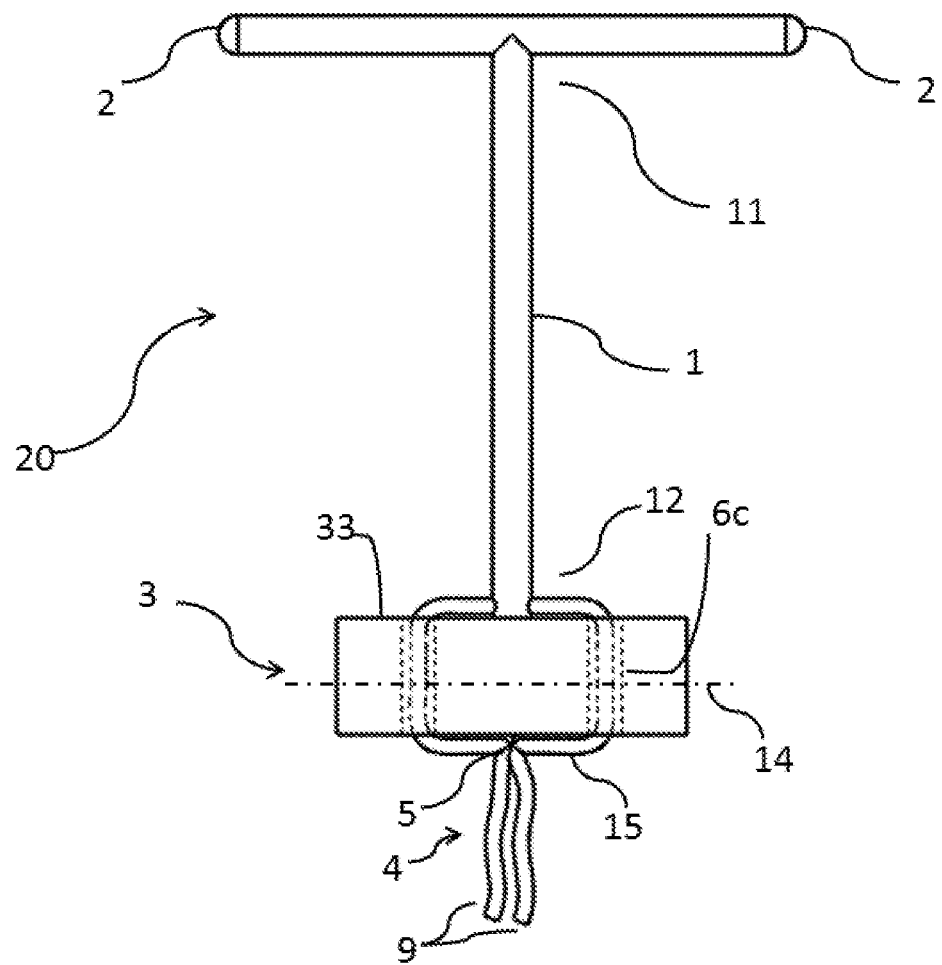
FIG. 5A illustrates IUD with a region being a cylinder and corresponding trajectory.
Figure 5B:
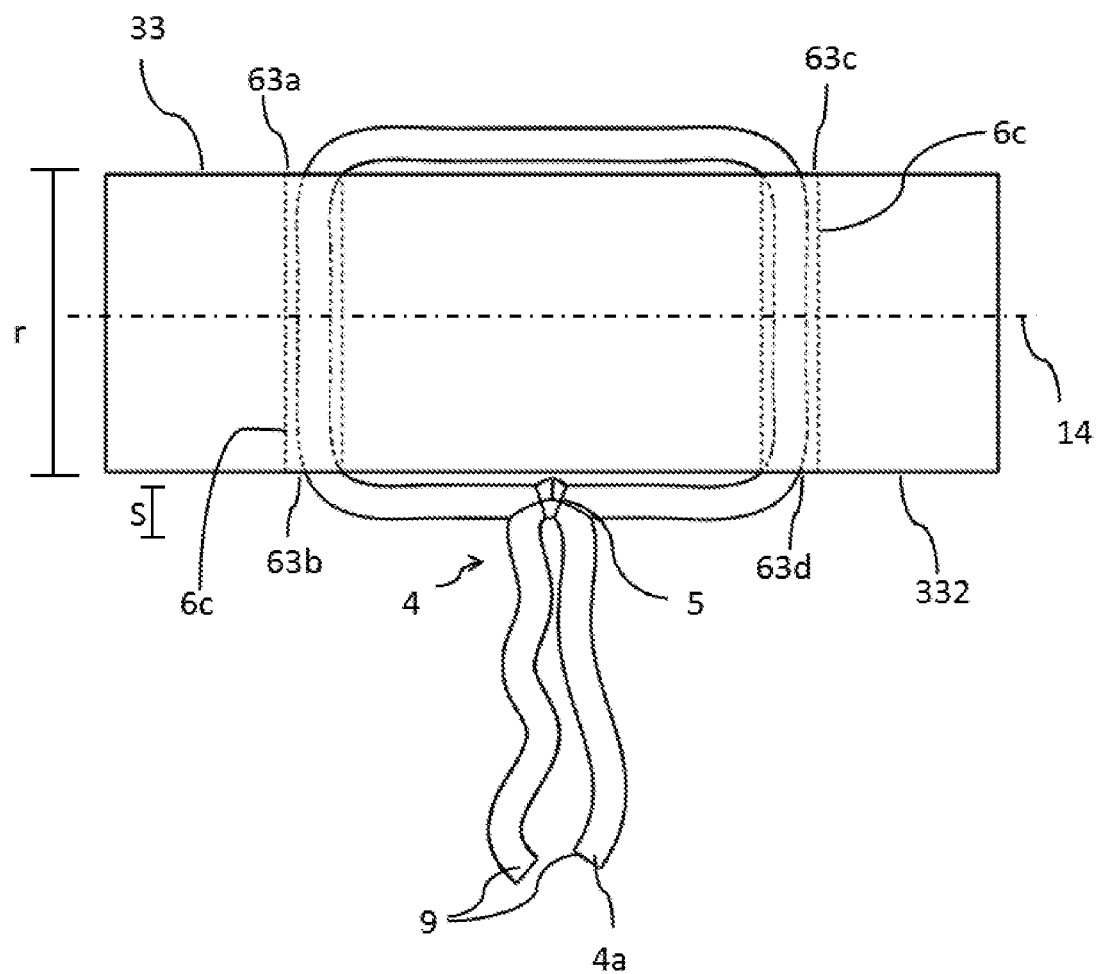
FIG. 5B gives further details of the cylinder and the trajectory which is a pair of parallel vertical closed channels.

According to FIG. 5A and 5B, the region (3) is a cylinder (33) present at the distal end (12) of the central vertical stem (1) of the IUD (20). The trajectory is a pair of parallel vertical closed channels (6c) through the region (3), each with a pair of openings (63a, 63b) and (63c, 63d) at both ends of the parallel vertical closed channels (6c). The first end (4a) of the string (4) of the IUD (20) is passed through the opening (63b) and retrieved from the opening (63a). The same first end (4a) of the string is then passed through the opening (63c) and is retrieved from the opening (63d). A knot (5) is tied tautly immediately below a surface (332) and in the middle of the cylinder (33).

Consequent to the shape of the cylinder (33) and the corresponding trajectory (6c), the length of the string (S) is shorter than the distance (r) of the region (3); and the loop (15) of the string, and therefore the knot (5) is unable to pivot around the axis (14).

Consequent to the shape of the cylinder (33), and the corresponding trajectory (6c), the knot (5) is NOT free to move from position in the middle of the opening (63b) and the opening (63d) to side wards as shown in FIG. 1D. In other words, the lateral shift of the knot (5) is restricted Consequent to restricted pivoting and lateral shift of the knot (5), the hanging portion (9) of the string continue to project downwards and do NOT develop tendency to get retracted and thus do NOT curl up in the uterus (16) through the cervix (17).

Figure 5C:
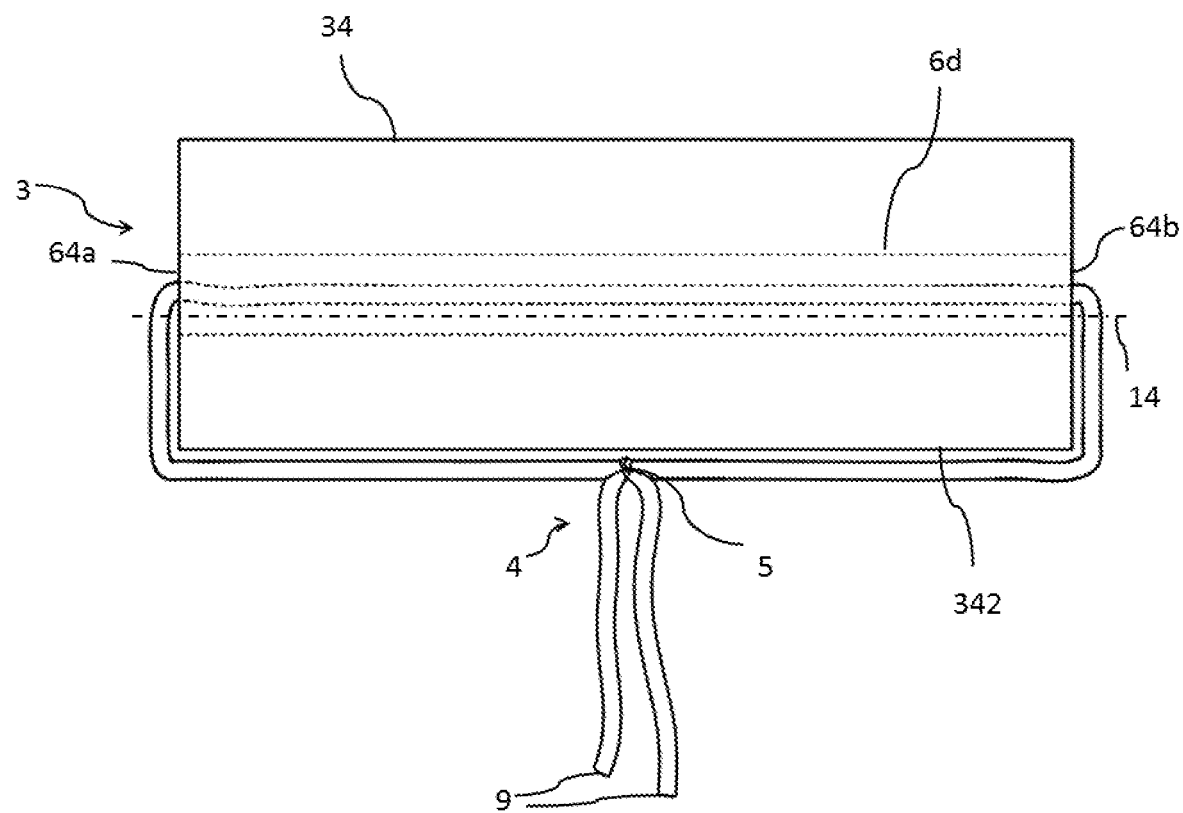
FIG. 5C illustrates another embodiment of an IUD with the region being a cylinder and trajectory of the string.

In another embodiment, referring to FIG. 5C, the region (3) is a cylinder (34) present at the distal end (12) of the central vertical stem (1) of the IUD (20). The trajectory is a closed channel (6d) with a pair of openings (64a, 64b) at the ends of the closed channel (6d), provided transversally to the central vertical stem (1) in the cylinder (34), through the closed channel (6d) and its axis (14) is parallel to the flat lower surface (342) of the cylinder (34). The string (4) is passed through the first opening (64a) of the channel (6d) and retrieved from a second opening (64b) of the channel and the knot (5) is tied keeping the string (4) taut, immediately below the flat lower surface (342) of the cylinder (34) and in the middle, leaving the hanging portion (9) of the strings (4) free.

Figure 5D:
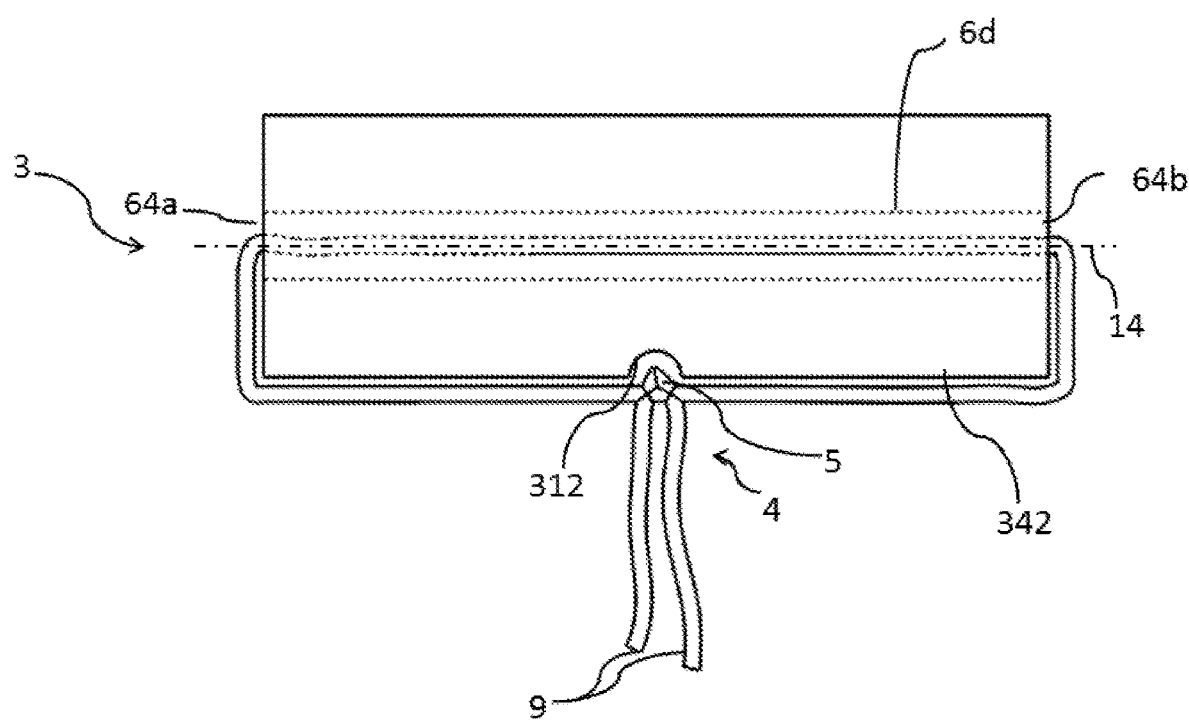
FIG. 5D illustrates another embodiment of an IUD with the region being a cylinder having a recess at the flat lower surface and trajectory of the string.

In another embodiment, the plurality of recess (312) is present on the surface (342) of the region (3) having differed shape and size. The recess provided on the surface of the region (3) retains the knot in the recess and thus restricts the lateral movement of the knot (5) as shown in FIG. 5D.

In another embodiment, wherever the string (4) is outside closed channels, an open channel is carved in the region.

Figure 6:
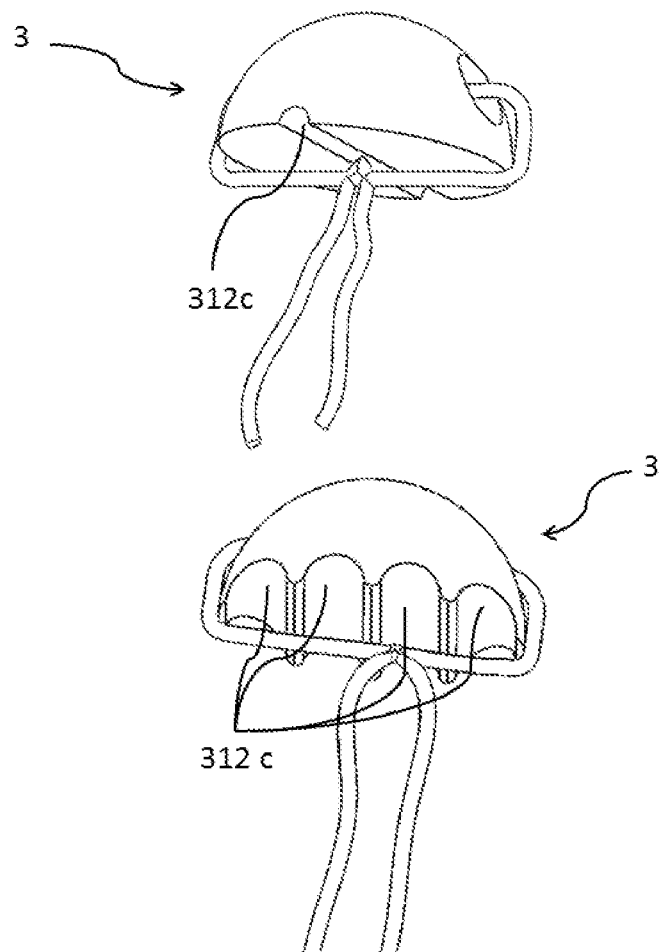
FIG. 6 shows plurality of open channels instead of plurality of recess as another embodiment.

In another embodiments, one or more recess shown in FIG. 3A, 3B, 3D, 5D can be open channels (312c) as shown in FIG. 6.

Figure 7A:
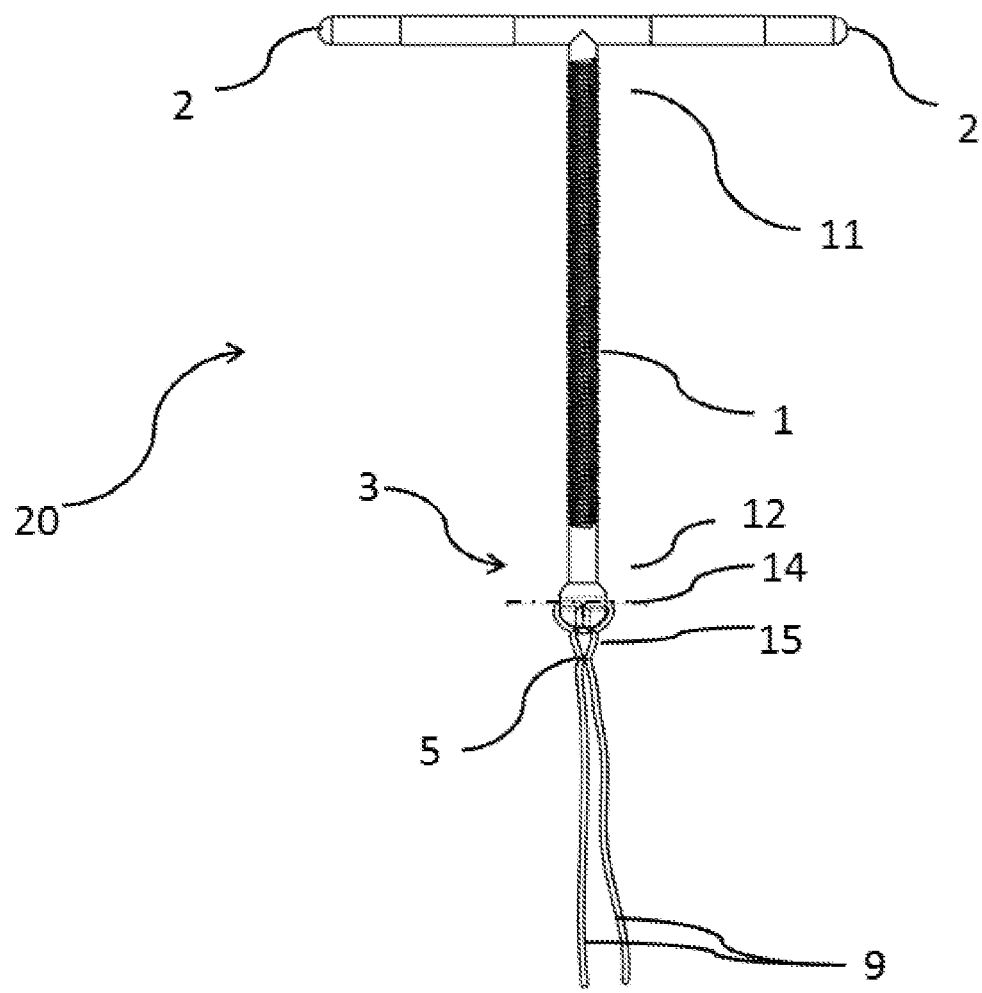
FIG. 7A illustrates an IUD where the region is a spheroid and trajectory is a "T" shape closed channel.
Figure 7B:
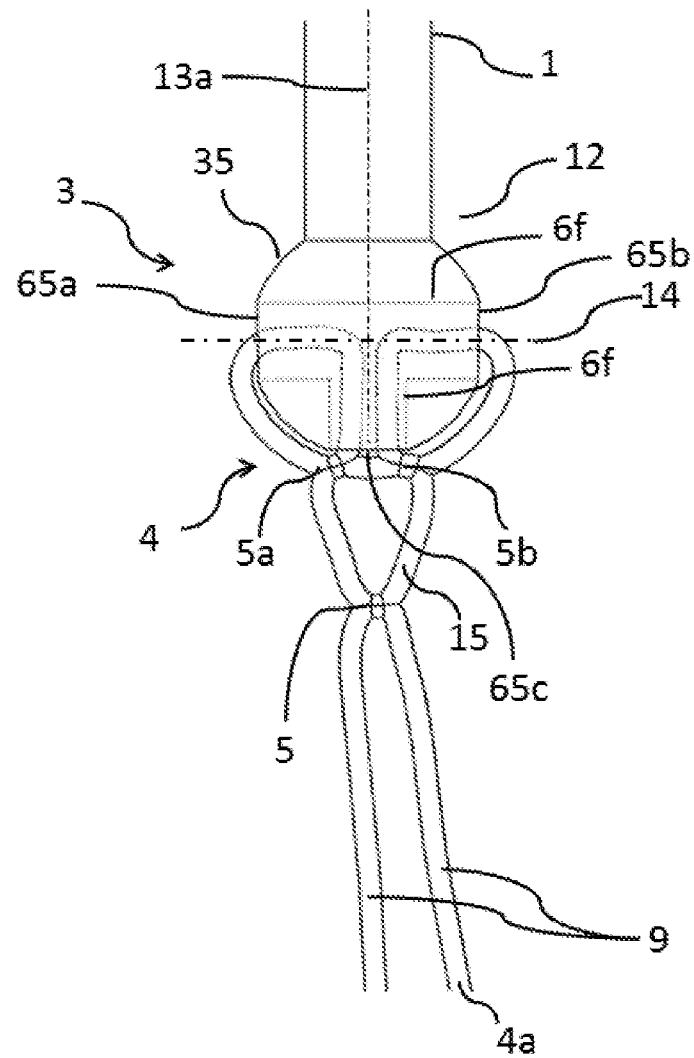
FIG. 7B gives further details of the trajectory and placement of the string in the trajectory.

In another embodiment, referring to FIG. 7A and 7B the region (3) is a spheroid (35) where trajectory is a closed channel (6f) in "T" shape, with three opening (65a, 65b and 65c) at the three ends of "T" shape of the closed channel (6f), an axis (14) of openings (65a, 65b) being transversal to the central vertical stem (1) and a middle opening (65c) substantially in a same axis (13a) as of the central vertical stem (1).

A first end (4a) of a string (4) is passed through the opening (65a) of the closed channel (6f) and retrieved from the middle opening (65c) of the closed channel (6f). A knot (5a) is tied in the vicinity of the middle opening (65c) keeping the string (4) taut as shown in FIG. 7B. The first end (4a) of the string (4) is again passed through the opening (65c) of the closed channel (6f) and retrieved from the opening (65b). Another knot (5b) is tied in the vicinity of the middle opening (65c) keeping the string (4) taut. Knot (5) tied now, keeping the string (4a) taut leaving the hanging portion (9) of the strings (4) free.

Figure 7C:
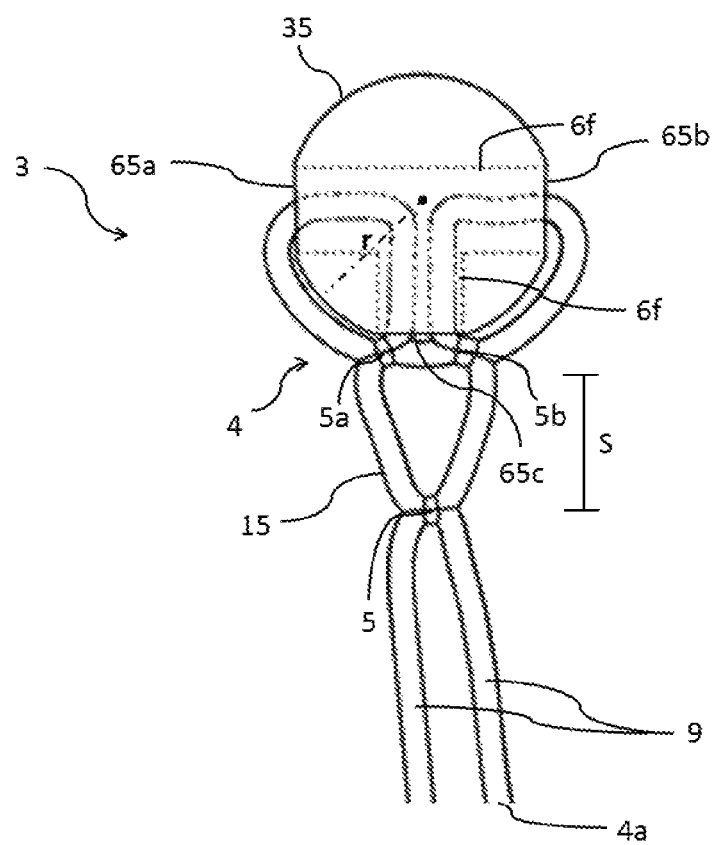
FIG. 7C gives closer view of the "T" shape closed channel and the string passing through the openings of the "T" shape closed channel.

Consequent to the shape of the spheroid (35) and the corresponding trajectory (6f) the length of the string (S) is shorter than the distance (r) of the region (3); and the loop (15) of the string and therefore the knot (5) is unable to pivot around the axis (14) as shown in FIG. 7C.

Consequent to the shape of the spheroid (35), and the corresponding trajectory (6f), the knot (5) is NOT free to move from the position in the middle of the opening (65c) to the side wards as shown in FIG. 1D. In other words, the lateral shift of the knot (5) is restricted.

Consequent to the restricted pivoting and the lateral shift of the knot (5), the hanging portion (9) of the string continue to project downwards and do NOT develop tendency to get retracted and thus do NOT curl up in the uterus (16) through the cervix (17).

Figure 8:
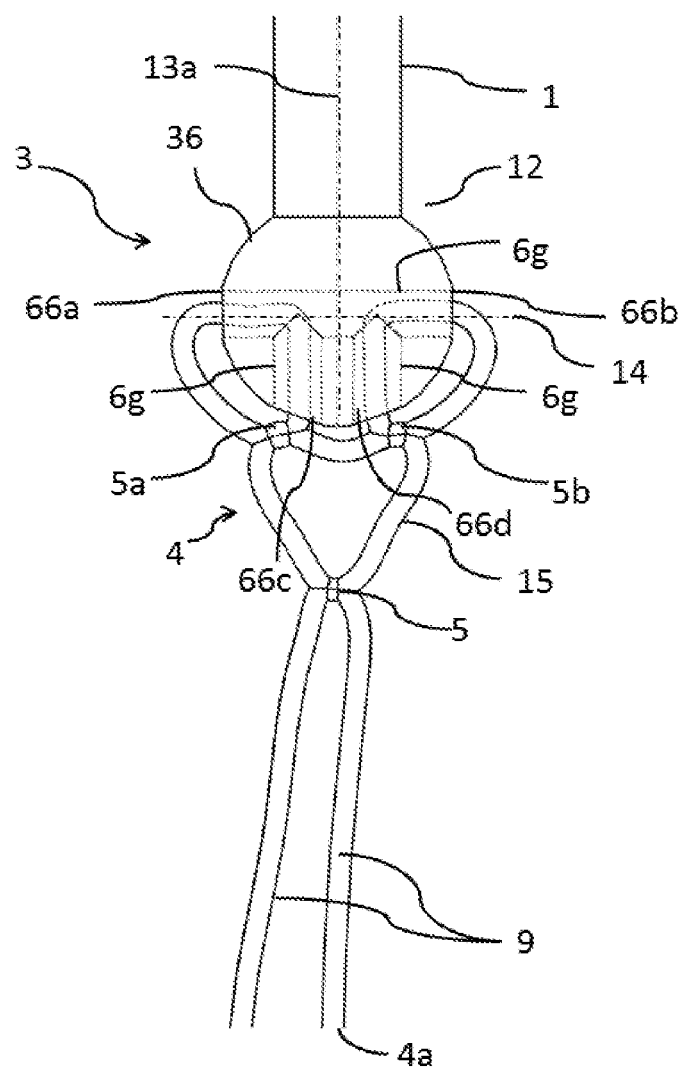
FIG. 8 illustrates another embodiment of an IUD with the region being a spheroid having a "π" shape closed channel and trajectory of the string.

In another embodiment, referring to FIG. 8 the region is a spheroid (36) where trajectory is a closed channel (6g) in a "π" shape, with four opening (65a, 65b, 65c and 65d) at the four ends of "π" shape of the closed channel (6g), an axis (14) of openings (65a, 65b) being transversal to the central vertical stem (1) and a middle openings (65c) and a middle opening (65d) on either side of the axis (13a) of the central vertical stem (1)

A first end (4a) of the string (4) is passed through the opening (66a) of the closed channel (6f) and retrieved from the middle opening (65c) of the closed channel (6f), a knot (5a) is tied in the vicinity of the middle opening (66c) keeping the string (4) taut as shown in FIG. 8B, the first end (4a) of the string (4) again passed through the opening (65d) of the closed channel (6f) and retrieved from the opening (65b). An other knot (5b) is tied in the vicinity of the middle opening (65d) keeping the string (4) taut. The knot (5) tied thereafter, keeping the string (4) taut leaving the hanging portion (9) of the strings (4) free.

Figure 9:
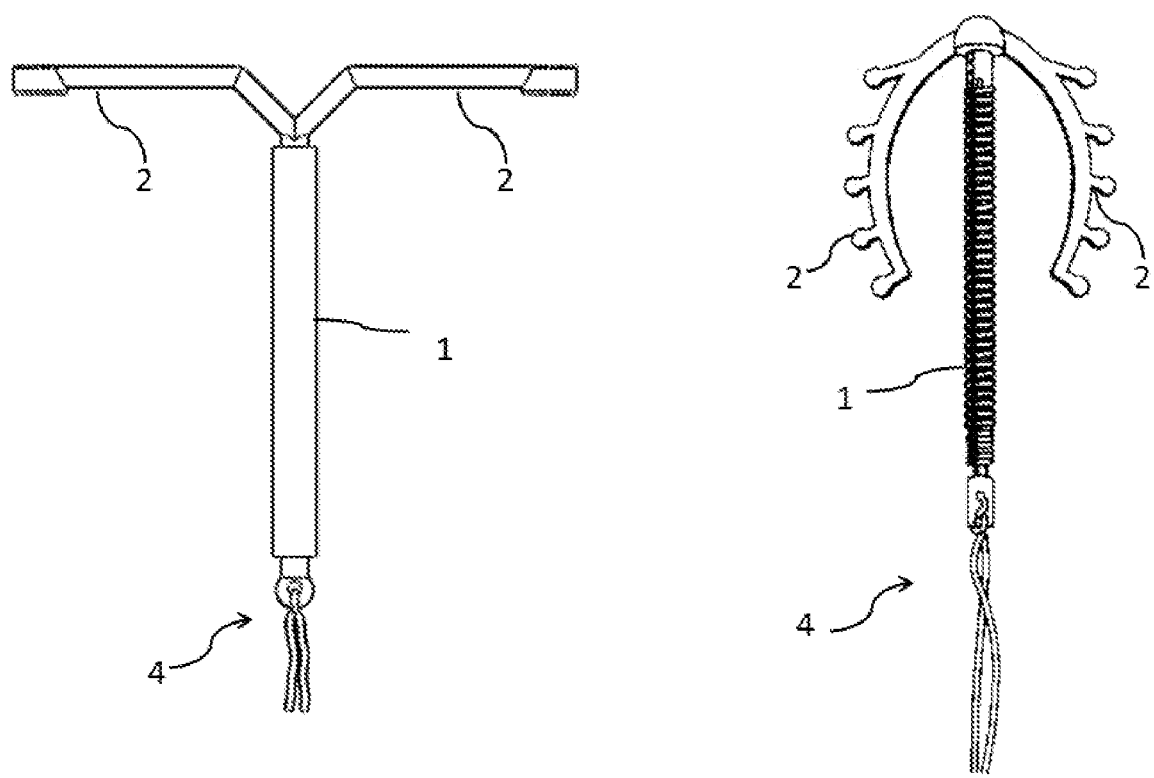
FIG. 9 illustrates the other shapes of the IUD wherein string is attached and knotted in a similar manner as above embodiment.

Such undesired curling of the string of the IUD can be restricted in a similar manner with different shapes and types of intra uterine devices and different shapes of the region whether copper or hormonal or medicinal as illustrated in FIG. 9.

We claim:

1. An intrauterine device (IUD) (20) comprising of: a central vertical stem (1) with a plurality of arms (2) attached to a proximal end (11) of the vertical stem (1); a region (3) attached to a distal end (12) of the vertical stem, wherein said region (3) is a hemisphere (31) having a flat lower surface (311) perpendicular to the central vertical stem (1); a trajectory in the hemisphere, wherein the trajectory is a closed channel (6a); a string (4) passed through the closed channel (6a); a pair of openings (61a, 61b) at the ends of the closed channel (6a), provided transversally to the central vertical stem (1) in the hemisphere (31); an axis (14) of the channel (6a) being parallel to a plane of the flat lower surface (311) of the hemisphere (31); a plane of the flat lower surface (311) makes an angle (18) with a tangent (19) at the end of the hemisphere (31) causing a sharp bend for the string (4); a knot (5) tied keeping the string (4) taut; a length (S) of the string (4) shorter than a distance (r) of the region (3), so as to restrict pivoting of a loop (15) and the knot (5) and so as to restrict lateral shift of the knot (5).

2. An intrauterine device (IUD) (20) comprising of: a central vertical stem (1) with a plurality of arms (2) attached to a proximal end (11) of the vertical stem (1); a region (3) attached to a distal end (12) of the vertical stem, wherein said region (3) is a hemisphere (31) having a flat lower surface (311) perpendicular to the central vertical stem (1) with a plurality of recess (312) present on the flat lower surface (311); wherein the plurality of recess (312) retains a plurality of knots (5) in the recess and restricting the lateral movement of the plurality of knots; a trajectory in the hemisphere, wherein the trajectory is a closed channel (6a); a string (4) passed through the closed channel (6a); a pair of openings (61a, 61b) at the ends of the closed channel (6a), provided transversally to the central vertical stem (1) in the hemisphere (31), an axis (14) of the channel (6a) being parallel to a plane of the flat lower surface (311) of the hemisphere (31); a plane of the flat lower surface (311) makes an angle (18) with a tangent (19) at the end of the hemisphere (31) causing a sharp bend for the string (4); a knot (5) tied keeping the string (4) taut; a length (S) of the string (4) shorter than a distance (r) of the region (3), so as to restrict pivoting of a loop (15) and the knot (5) and so as to restrict lateral shift of the knot (5).

3. An intrauterine device (IUD) (20) comprising of: a central vertical stem (1) with a plurality of arms (2) attached to a proximal end (11) of the vertical stem (1); a region (3) attached to a distal end (12) of the vertical stem, wherein the region (3) is a sphere (32) present at the distal end (12) of the central vertical stem (1) of the IUD (20); a trajectory in the sphere, wherein the trajectory is a triangular closed channel (6b) with a three pairs of openings (62a, 62b), (62c, 62d) and (62e, 62f) at a three ends of the triangular closed channel (6b) in the sphere (32), an axis (14) of openings (62a, 62b) being transversal to the central vertical stem (1); a middle of the opening (62e) and opening (62d) substantially in a same axis (13a) as of the central vertical stem (1); a string (4) passed through the triangular closed channel (6b); a knot (5) tied keeping the string (4) taut; a length (S) of the string (4) shorter than a distance (r) of the region (3), so as to restrict pivoting of a loop (15) and the knot (5) and so as to restrict lateral shift of the knot (5).

4. An intrauterine device (IUD) (20) comprising of: a central vertical stem (1) with a plurality of arms (2) attached to a proximal end (11) of the vertical stem (1); a region (3) attached to a distal end (12) of the vertical stem, wherein said region (3) is a cylinder (33) present at the distal end (12) of the central vertical stem (1) of the IUD (20); a trajectory in the cylinder, wherein the trajectory is a pair of parallel vertical closed channels (6c) through the region (3), each with a pair of openings (63a, 63b) and (63c, 63d) at both ends of the parallel vertical closed channels (6c) of the cylinder (33); a string (4) passed through the triangular closed channel (6b); a knot (5) tied keeping the string (4) taut; a length (S) of the string (4) shorter than a distance (r) of the region (3), so as to restrict pivoting of a loop (15) and the knot (5) and so as to restrict lateral shift of the knot (5).

5. An intrauterine device (IUD) (20) comprising of: a central vertical stem (1) with a plurality of arms (2) attached to a proximal end (11) of the vertical stem (1); a region (3) attached to a distal end (12) of the vertical stem, wherein said region (3) is a cylinder (34) present at the distal end (12) of the central vertical stem (1) of the IUD (20); a trajectory is a closed channel (6d) with a pair of openings (64a, 64b) at the ends of the closed channel (6d), provided transversally to the central vertical stem (1) in the cylinder (34), through the closed channel (6d); an axis (14) of the pair of openings (64a, 64b) is parallel to a flat lower surface (342) of the cylinder (34); a string (4) passed through the closed channel; a knot (5) tied keeping the string (4) taut; a length (S) of the string (4) shorter than a distance (r) of the region (3), so as to restrict pivoting of a loop (15) and the knot (5) and so as to restrict lateral shift of the knot (5).

6. An intrauterine device (IUD) (20) comprising of: a central vertical stem (1) with a plurality of arms (2) attached to a proximal end (11) of the vertical stem (1); a region (3) attached to a distal end (12) of the vertical stem, wherein said region (3) is a spheroid (35) present at the distal end (12) of the central vertical stem (1) of the IUD (20); a trajectory is a closed channel (6f) in "T" shape with three opening (65a, 65b and 65c) at the three ends of "T" shape of the closed channel (6f), an axis (14) of openings (65a, 65b) being transversal to the central vertical stem (1); a middle opening (65c) substantially in a same axis (13a) as of the central vertical stem (1); a first end (4a) of a string (4) is passed through the opening (65 a) of the closed channel (6f) and retrieved from the middle opening (65c) of the closed channel (6f), a first knot (5a) is tied in the vicinity of the middle opening (65c) keeping the string (4) taut; the first end (4a) of the string (4) again passed through the opening (65c) of the closed channel (6f) and retrieved from the opening (65b); a second knot (5b) is tied in the vicinity of the middle opening (65c) keeping the string (4) taut; a third knot (5) tied thereafter, keeping the string (4) taut; a length (S) of the string (4) shorter than a distance (r) of the region (3), so as to restrict pivoting of a loop (15) and the knot (5) and so as to restrict lateral shift of the knot (5).

7. An intrauterine device (IUD) (20) comprising of: a central vertical stem (1) with a plurality of arms (2) attached to a proximal end (11) of the vertical stem (1); a region (3) attached to a distal end (12) of the vertical stem, wherein said region (3) is a spheroid (36) present at the distal end (12) of the central vertical stem (1) of the IUD (20); a trajectory is a closed channel (6g) in "π" shape with four opening (66a, 66b, 66c and 66d) at four ends of the "π" shape of the closed channel (6g), an axis (14) of openings (66a, 66b) being transversal to the central vertical stem (1); a first middle openings (66c) and a second middle opening (66d) on either side of the axis (13a) of the central vertical stem (1); a first end (4a) of a string (4) is passed through the opening (66a) of the closed channel (6f) and retrieved from the first middle opening (66c) of the closed channel (6g), a first knot (5a) is tied in the vicinity of the first middle opening (66c) keeping the string (4) taut; the first end (4a) of the string (4) again passed through the opening (66d) of the closed channel (6f) and retrieved from the opening (66b); a second knot (5b) is tied in the vicinity of the second middle opening (66d) keeping the string (4) taut; a third knot (5) tied thereafter, keeping the string (4) taut; a length (S) of the string (4) shorter than a distance (r) of the region (3), so as to restrict pivoting of a loop (15) and the knot (5) and so as to restrict lateral shift of the knot (5).

* * * * *